(12) United States Patent
Zengerle et al.

(10) Patent No.: US 6,280,148 B1
(45) Date of Patent: Aug. 28, 2001

(54) MICRODOSING DEVICE AND METHOD FOR OPERATING SAME

(75) Inventors: Roland Zengerle, München; Michael Freygang, VS-Villingen; Manfred Stehr; Stephan Messner, both of VS-Schwenningen; Matthias Ashauer, Unterkirnach; Rainer Rossberg, VS-Villingen, all of (DE)

(73) Assignee: Hahn-Schickard-Gesellschaft fur Angewandte Forschung (DE)

( * ) Notice: Subject to any disclaimer, the term of this patent is extended or adjusted under 35 U.S.C. 154(b) by 0 days.

(21) Appl. No.: 09/367,664

(22) PCT Filed: Feb. 5, 1998

(86) PCT No.: PCT/EP98/00617

§ 371 Date: Jan. 31, 2000

§ 102(e) Date: Jan. 31, 2000

(87) PCT Pub. No.: WO98/36832

PCT Pub. Date: Aug. 27, 1998

(30) Foreign Application Priority Data

Feb. 19, 1997 (DE) ................................ 197 06 513
Jan. 22, 1998 (DE) ................................ 198 02 367

(51) Int. Cl.[7] ............................ F04B 49/06; F04B 49/00; F04B 17/00
(52) U.S. Cl. .................... 417/44.1; 417/212; 417/413.2; 417/413.3
(58) Field of Search ...................... 417/44.1, 212, 417/413.2, 413.3

(56) References Cited

U.S. PATENT DOCUMENTS 5,085,562 * 2/1992 Van Lintel ..................... 417/413.3

(List continued on next page.)

FOREIGN PATENT DOCUMENTS 0439327 1/1991 (EP) .

(List continued on next page.)

OTHER PUBLICATIONS

Schwesinger N., "Planare Titenstrahldruckkopf Mit Piezokeramischem Antrieb", F & M Feinwerktechnik Mikrotechnik published Nov. 1993.

(List continued on next page.)

Primary Examiner—Charles G. Freay
Assistant Examiner—Michael K. Gray
(74) Attorney, Agent, or Firm—Beyer Weaver & Thomas, LLP

(57) ABSTRACT

A microdosing device comprises a pressure chamber which is at least partly delimited by a displacer, an actuating device for actuating the displacer, the volume of the pressure chamber being adapted to be changed by actuating the displacer, a media reservoir which is in fluid comunication with the pressure chamber via a first fluid line, and an outlet opening which is in fluid communication with the pressure chamber via a second fluid line. The microdosing device additionally comprises a means for detecting the respective position of the displacer and a control means which is connected to the actuating device and to the means for detecting the position of the displacer, said control means controlling the actuating device on the basis of the detected position of the displacer or on the basis of displacer positions detected during at least one preceding dosing cycle so as to cause the discharge of a defined volume of fluid from the outlet opening. The control means comprises means for controlling the actuating device with a signal of low edge steepness so as to cause the displacer to move from a first position to a predetermined second position, the second position of the displacer defining a larger volume of the pressure chamber than the first position. In addition, the control means comprises means for controlling the actuating device with a signal of high edge steepness so as to cause the displacer to move from the second position to the first position for discharging in this way a defined volume of fluid from the outlet opening.

21 Claims, 5 Drawing Sheets

U.S. PATENT DOCUMENTS

| | | | |
|---|---|---|---|
| 5,096,388 | * | 3/1992 | Weinberg .......................... 417/413.3 |
| 5,190,522 | * | 3/1993 | Wojcicki et al. ...................... 604/65 |
| 5,205,819 | | 4/1993 | Ross et al. .............................. 604/67 |
| 5,224,843 | * | 7/1993 | Van Lintel ........................ 417/413.2 |
| 5,271,724 | * | 12/1993 | Van Lintel ........................ 417/413.2 |
| 5,277,556 | * | 1/1994 | Van Lintel ........................ 417/413.2 |
| 5,342,176 | * | 8/1994 | Redlich ................................ 417/212 |
| 5,593,290 | | 1/1997 | Greisch et al. ...................... 417/478 |
| 5,759,014 | * | 6/1998 | Van Lintel ........................ 417/413.3 |

FOREIGN PATENT DOCUMENTS

| | | |
|---|---|---|
| 0725267 | 1/1996 | (EP) . |
| 0810438 | 12/1997 | (EP) . |
| 2650634 | 2/1991 | (FR) . |

OTHER PUBLICATIONS

A. Jahns, "Pipettieren und Dispersieren", Jahrgang 8, 1993.

Bentin et al., "Physical Properties of Micro–Planar Ink–Drop Generators", Jun. 1986, vol. 12, No. 3, Journal of Imaging Technology.

W. Wehl, "Tintendrucktechnologie: Paradigma Und Motor der Mikrosystemtechnik" Mikrosystemtechnik published Sep. 1995.

"Technologiepreis Hamburg 1990", Gestiftet von der Commerzbank Hamburg.

R. Zengerie, "Mikrosysteme—Chancen Fur die Dosiertechnki", Jan. 1996, Wagen + Dosieren.

H. Bentin et al., "Physical Properties of Micro–Planar Ink–Drop Generators", Journal of Imaging Technology, vol. 12, No. 3, pp. 152–155, Jun. 1986.*

* cited by examiner

MICRODOSING DEVICE AND METHOD FOR OPERATING SAME

BACKGROUND OF THE INVENTION

1. Field of the Invention

The present invention relates to a microdosing device and to a method for operating the same.

2. Description of Prior Art

Precise dosing of extremely small volumes of liquid in the range between 0.01 $\mu$l and 1 $\mu$l is of great and decisive importance e.g. in the fields of biotechnology, DNA analytical chemistry and combinatorial chemistry. According to the prior art, dispensers or pipettes are predominantly used for dosing small volumes. The volume to be dosed is in these cases displaced either directly, by a so-called piston-type direct displacement, or via an intermediate air cushion. In this respect, reference is made e.g. to the article "Pipettieren und Dispensieren", A. Jahns, Fachzeit-schrift der Technischen Assistenten in der Medizin, volume 8 (1993), No. 12, pp. 116–1172, Umschau Zeitschriftenverlag.

Air-cushion pipettes are suitable for dosing volumes between 0.01 $\mu$l and 5 ml, accuracies of ±2–3% being achieved when the volumes exceed 1 $\mu$l. In the case of smaller volumes, however, only accuracies of approx. ±10% are achieved due to surface effects at the tip of the pipette. The limited dosing accuracy in the case of smaller volumes is predominantly due to the fact that the tip of the pipette or dispenser must be immersed in the medium to be dosed, whereby the dosing amount is influenced by effects such as surface tension, wetting and hydrostatic pressure. In order to avoid these problems as well as the risk of carrying over media due to immersion, a dosing system should be based on the discharge of the dosed volume in a free jet. Direct-diplacement dispensing devices offer this additional advantage, but only in the case of volumes of approx. 10 $\mu$l and more.

Known systems discharging very small volumes of liquid in a free jet are ink-jet printheads. Ink-jet printheads are known which are based on two fundamentally different principles, viz. those which are effective making use of thermal transducers and those which are effective making use of piezoelectric transducers. In this respect, reference is made to the publications N. Schwesinger: "Planarer Tintenstrahldruckkopf". F&M, 11–12; pp. 456–460; 1993; H. Bentin, M. Doering, W. Radtke, U. Rothgordt: "Physical Properties of Micro-Planar Ink-Drop Generators". J. Imaging Technology, 3; pp. 152–155; 1986; and Wolfgang Wehl; Tintendrucktechnologie; Paradigma und Motor der Mikrosystemtechnik; Feinwerktechnik & Meßtechnik; Teil 1 in Ausgabe 6/95, Teil 2 in Ausgabe 9/95.

When printheads operating according to the "drop-on-demand" principle are used, a small ink drop is flung in a free jet onto a paper after the application of a voltage pulse. A typical drop diameter is approx. 60 $\mu$m, i.e. the volume is approx. 0.0001 $\mu$l. Normally, these printheads are, however, only adapted to be used in combination with special inks. Media which are used e.g. in the field of biotechnology are in most cases extremely different from these inks as far as viscosity and surface tension are concerned. The viscosity and the surface tension are, however, factors which substantially influence the size of the drops and, consequently, the volume dosed. Furthermore, generation of drops is only possible in a very limited viscosity range. The volume of the individual drops can, moreover, only be modified in a very restricted range by modifying the control pulses.

Furthermore, dosing systems are known, which are also capable of generating drops in the case of media having strongly different viscosities. Such a system is described e.g. in the publication "Mikrodosierung", company publication of the firm of microdrop GmbH, Norderstedt, 1995. As in the case of ink-jet printheads, the drop volume produced in these systems is determined mainly by the size of the nozzle diameter. Only to a very limited extent can it also be influenced by the electric control of the actuator. As in the case of ink-jet printheads, the process of drop interruption at the nozzle depends, however, on the physical properties, i.e. the viscosity, the surface tension, etc. of the media to be dosed. The exact size of the drops is therefore again strongly media-dependent. The dosing of a desired volume, which ranges between 0.1 $\mu$l and 1 $\mu$l in most cases, is based the counting of individual drops of the same size. The typical volume of an individual drop is smaller than 0.001 $\mu$l. Since the volume errors of the individual drops will, however, accumulate in this process, the dosing accuracy is strongly limited.

In order to permit an increase of this dosing accuracy, complicated systems are necessary. An image processor can, for example, be used by means of which the size of the individual drops can be determined and the number of drops required can be calculated during the dosing process. According to an alternative method of increasing the dosing accuracy, a fluorescent substance can be admixed to the medium to be dosed. In the case of this alternative method, the dosing process will be finished when the intensity of the fluorescent signal has reached the set value. It is, however, apparent that the above-mentioned methods of increasing the dosing accuracy are both very complicated and expensive.

EP-A-0439327 describes a control system for a micropump, which is adapted to be used e.g. in a dosing device. The control system selectively controls the generation of drive pulses so as to control the discharge of fluid through the pump. According to the known control system, fluctuations of potential of the piezoelectric driver element of the micropump are detected so as to find out whether or not the pump operates properly so that operation of the pump can be stopped and the micropump can be replaced, if necessary.

U.S. Pat. No. 5,205,819 discloses an infusion pump for dosing liquids, e.g. when liquids are being infused into the human body. The disclosed infusion pump comprises a pressure chamber which is partly delimited by a membrane. A piezo-electric component is provided for actuating the membrane. The pressure chamber is adapted to be connected to a liquid reservoir via an inlet line and to an outlet opening via an outlet line. A control unit is provided for controlling the piezoelectric component; the infusion pump can additionally be provided with detection electrodes providing signals which indicate the degree of bending of the membrane. These detection electrodes serve, on the one hand, the purpose of indicating error conditions caused by air bubbles in the pump chamber or by a clogged outlet line. During normal operation, the detection electrodes may, on the other hand, serve the purpose of providing an output signal representing a measure of the liquid volume dosed in the case of each actuation of the membrane. In order to provide a pre-determined flow rate, the control unit is programmed for adjusting the pulse frequency for the actuation of the piezoelectric component in dependence upon the signal amplitude of the output signal of the detection electrodes. The known infusion pump is driven by a sequence of pulses consisting each of positive and negative pulses having the same amplitude and duration, the frequency of the sequence of pulses being controlled in accordance with the necessary flow rate.

SUMMARY OF THE INVENTION

It is the object of the present invention to provide an uncomplicated microdosing device permitting the discharge of exactly defined volumes of fluid.

In accordance with a first aspect of the present invention, this object is achieved by a microdosing device comprising:
- a pressure chamber which is at least partly delimited by a displacer;
- an actuating device for actuating the displacer, the volume of the pressure chamber being adapted to be changed by actuating the displacer;
- a media reservoir which is in fluid comunication with the pressure chamber via a first fluid line;
- an outlet opening which is in fluid communication with the pressure chamber via a second fluid line;
- a means for detecting the position of the displacer; and
- a control means which is connected to the actuating device and to the means for detecting the position of the displacer and which controls the actuating device on the basis of the detected position of the displacer or on the basis of displacer positions detected during at least one preceding dosing cycle so as to cause the discharge of a defined volume of fluid from the outlet opening,
- wherein the control means comprises means for controlling the actuating device with a signal of low edge steepness so as to cause the displacer to move from a first position to a predetermined second position, the second position of the displacer defining a larger volume of the pressure chamber than the first position, and
- wherein the control means comprises means for controlling the actuating device with a signal of high edge steepness so as to cause the displacer to move from the second position to the first position for discharging in this way a defined volume of fluid from the outlet opening.

It is a further object of the present invention to provide an uncomplicated pipetting device permitting exactly defined volumes of fluid to be sucked in and discharged.

In accordance with a second aspect of the present invention, this object is achieved by a pipetting device comprising:
- a pressure chamber which is at least partly delimited by a displacer;
- an actuating device for actuating the displacer the volume of the pressure chamber being adapted to be changed by actuating the displacer;
- an outlet opening which is in fluid communication with the pressure chamber via a fluid line;
- a means for detecting the position of the displacer; and
- a control means which is connected to the actuating device and to the means for detecting the position of the displacer and which controls the actuating device on the basis of the detected position of the displacer or on the basis of displacer positions detected during at least one preceding pipetting cycle so as to cause a defined volume of fluid to be sucked in through and/or discharged from the outlet opening,
- wherein the control means comprises means for controlling the actuating device with a signal of low edge steepness so as to cause the displacer to move from a first position to a predetermined second position, the second position of the displacer defining a larger volume of the pressure chamber than the first position, and
- wherein the control means comprises means for controlling the actuating device with a signal of high edge steepness so as to cause the displacer to move from the second position to the first position for discharging in this way a defined volume of fluid from the outlet opening.

It is still a further object of the present invention to provide a method of operating such a microdosing device.

In accordance with a third aspect of the present invention, this object is achieved by a method of operating a microdosing device according to the present invention comprising the steps of controlling the actuating device with a signal of low edge steepness so as to cause the displacer to move from a first position to a predetermined second position, the second position of the displacer defining a larger volume of the pressure chamber than the first position, and, subsequently, controlling the actuating device with a signal of high edge steepness so as to cause the displacer to move from the second position to the first position for discharging in this way a defined volume of fluid from the outlet opening.

When the microdosing device is put into operation for the first time, the pressure chamber and the fluid lines are first filled with a fluid before the actuating device is controlled with the signal of low edge steepness.

The microdosing device according to the present invention can be produced in an advantageous manner making use of micromechanical methods, especially methods in the field of semiconductor technology. Furthermore, the microdosing device according to the present invention can have a modular structural design of such a nature that e.g. the pressure chamber, the displacer, the means for detecting the position of the displacer and, optionally, at least parts of the first and of the second fluid line are implemented as a replaceable module by means of micromechanical methods.

In the case of the present invention, the position of the displacer is preferably detected by integrated sensors. A respective displacer position corresponds to a defined volume of the pressure chamber. Knowing the volume of the pressure chamber, the control means is therefore capable of controlling the actuating means for moving the displacer in such a way that the discharge of a defined volume of fluid from the discharge opening will be caused. The essential advantage of such a dosing process making use of an integrated volume measurement is to be seen in the fact that a fluid jet as a whole is discharged, without any necessity of adding a plurality of individual drops for obtaining the desired dosing volumes, e.g. in the field of biotechnology. Although the exact interruption of the free jet at the outlet opening is influenced by the properties of the medium, as in the case of conventional systems, a higher dosing accuracy is still achieved according to the present invention. Due to the fact that also larger volumes in the desired range between 0.01 $\mu$l and 1 $\mu$l can be discharged during an operation by the media displacer of the microdosing device according to the present invention, volume errors, which result from the interruption of the individual drops and which would amount to a large relative error if drop volumes of 0.0001 $\mu$l were discharged, are no longer of any importance. A summation of the systematic errors per drop no longer occurs according to the present invention.

When the displacer is being returned to the second position, whereby the volume of the pressure chamber is reduced, so as to eject the fluid through the outlet opening in the form of a free jet, the movement of the fluid in the first fluid line, i.e. the reservoir channel, and in the second fluid line, i.e. the nozzle channel, is determined almost exclusively by the relation between the fluid inertias in the respective fluid lines, the relation between the flow resistances of the fluid lines being, however, negligible. The defined volume of fluid, which is ejected by means of the microdosing device according to the present invention, is therefore almost independent of the viscosity, surface tensions, etc. of the medium to be dosed. Hence, the present invention can be used for dosing media of different viscosities and surface tensions, which are used e.g. in the field of biotechnology.

In the case of the dosing method according to the present invention a jet of fluid, or if the device is used for liquids, a jet of liquid having a variable, adjustable volume is produced by a media displacer, the volume of the jet of liquid being controlled via a volume sensor integrated in the media displacer in the case of a preferred embodiment. The volume sensor detects the current displacement state of the media displacer and outputs an electric signal indicative of this displacement state. The control evaluates the development of the time-dependent displacement process detected by the volume sensor and controls the actuator of the displacer.

Optionally, the microdosing device according to the present invention can comprise additional elements, e.g. additional sensors for measuring the pressure development in the pressure chamber, which can also be referred to as dosing chamber, the temperature of the medium, etc., so that additional physical influences can be taken into account in the control of the dosing process. Furthermore, an active or a passive valve can be installed in the reservoir channel for preventing a return flow of the medium from the pressure chamber to the reservoir.

The microdosing device according to the present invention can also be used for pipetting a fluid or a liquid. For this purpose, a fluid is sucked in via the outlet opening, which can also be referred to as nozzle, e.g. by immersing the nozzle into a fluid to be pipetted. Subsequently, the sucked-in fluid is discharged in a fee jet in the manner described. The sucking in can be effected e.g. by a vacuum in the media reservoir, which causes the fluid to be sucked in, or by a suitable movement of the actuator.

The present invention additionally provides a pipetting device in the case of which the fluid can be sucked through the outlet opening into the dosing chamber by means of a suitable movement of the actuator. The structural design of the pipetting device corresponds essentially to that of the microdosing device according to the present invention, the media reservoir and the fluid line connecting the media reservoir to the dosing chamber being, however, not provided in the pipetting device.

The microdosing device according to the present invention can be used in an advantageous manner for forming an array of microdosing devices in which several microdosing devices are arranged side by side and adapted to be addressed individually. Also the pipetting device according to the present invention can be used in the same way for providing an array of micropipetting devices.

Further developments of the present invention are disclosed in the dependent claims.

BRIEF DESCRIPTION OF THE DRAWINGS

In the following, preferred embodiments of the present invention will be explained in detail making reference to the drawings enclosed, in which.

DESCRIPTION OF PREFERRED EMBODIMENTS OF THE INVENTION

Figure 1:
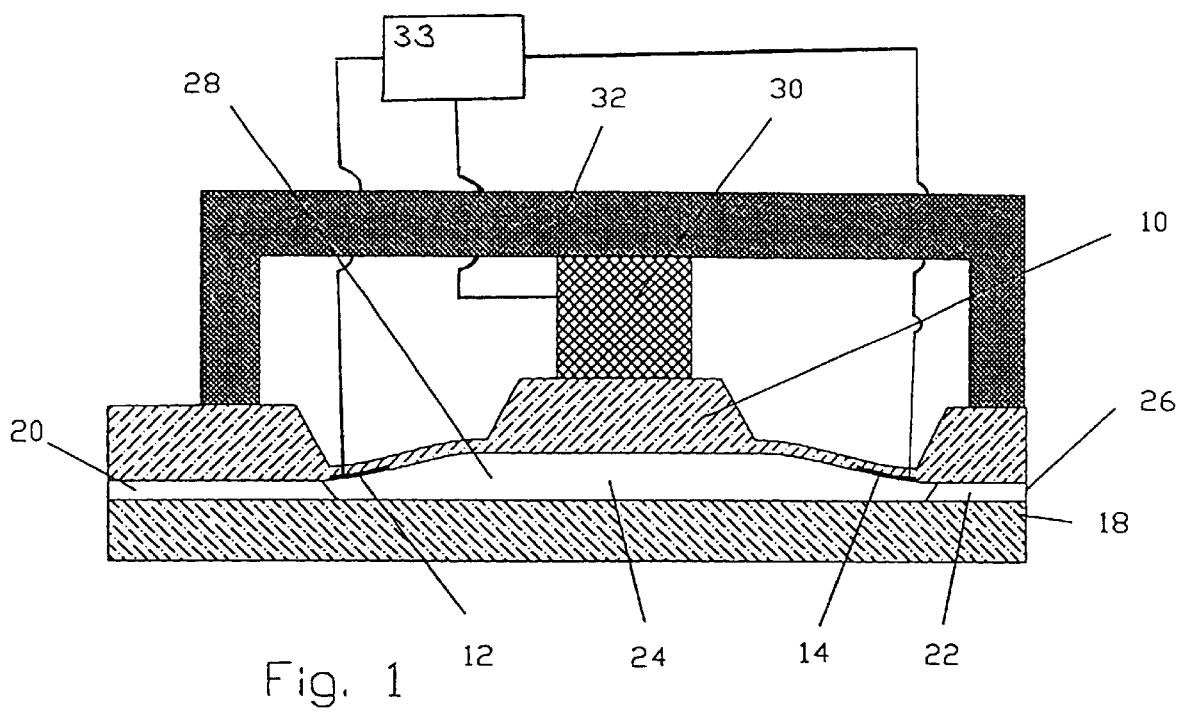
FIG. 1 shows a schematic cross-sectional representation of components of a preferred embodiment of the microdosing device according to the present invention.

FIG. 1 shows a possible embodiment of the microdosing device according to the present invention, which is particularly suitable for producing the dosing element by means of semiconductor-technological methods. In the embodiment shown the media displacer 10 is realized as a stiffened membrane which is etched in silicon. In this embodiment, the volume sensor consists of piezoresistive resistors 12 and 14 which are integrated in the media displacer. The mechanical stress resulting from a specific displacer position at the location of the resistors 12 and 14 in the media displacer 10 is converting into an electric signal via the piezoresistive effect. Thus, the resistors 12 and 14 represent means for detecting the position of the displacer.

Figure 2:
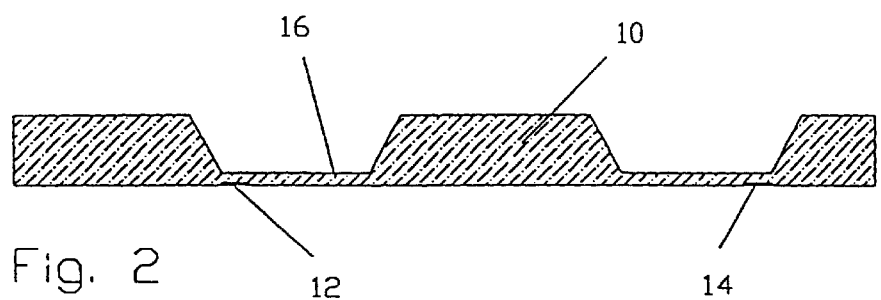
FIG. 2 shows a schematic cross-sectional representation of the displacer used in the embodiment shown in FIG. 1.

FIG. 2 shows an enlarged cross-sectional view of the displacer structure 10. The displacer structure shown in FIG. 2 is produced by means of anisotropic KOH etching resulting in the trapezoidal recesses which define the membrane 16.

In the embodiment of the present invention shown in FIG. 1, the displacer structure 10 is connected to a Pyrex™ glass plate 18 by means of anodic bonding. In the preferred embodiment, recesses are provided in the silicon wafer in which the displacer structure 10 is defined, the recesses defining a reservoir channel 20, a nozzle channel 22 as well as a pressure chamber 24. The nozzle channel 22 is in fluid communication with an outlet opening 26, which is indicated by broken lines in FIG. 1. The outlet opening 26 can be implemented in the form of a nozzle. The reservoir channel 20 is in fluid communication with a media reservoir (not shown). The pressure chamber 24 defines a dosing volume 28 which is adapted to be controlled by a movement of the displacer. In the embodiment shown in FIG. 1, a piezoelectric actuating device, which is a piezo-stack actuator 30 in this embodiment, is attached via an abutment 32 t the central stiffened area of the displacer in such a way that the media displacer 10 can be moved by actuating the piezo stack 30.

The piezoresistive resistors 12 and 14 as well as the piezostack 30 are electrically connected to a control means 33.

The pressure or dosing chamber 24, the fluid lines 20, 22 and the outlet opening 26 can be produced in the silicon wafer e.g. by standard etching techniques. The dosing chamber and the fluid lines can be sealed hermetically by connecting the silicon wafer to a Pyrex™ plate (glass) by means of anodic bonding. Alternatively, a piezo bending transducer or a piezo plate could be used as a drive means apart from the piezo-stack actuator shown. It is, however, apparent that the present invention is not limited to piezoelectric drive means, but that also other drive means, such a electromagnetic or electrostatic ones, can be used.

The reservoir channel, the pressure chamber, the nozzle channel and the displacer membrane are preferably produced by anisotropic KOH etching leading to trapezoidal or triangular channel cross-sections. It is, however, also possible to use other arbitrary cross-sectional shapes, e.g. trenches with vertical walls which are produced by dry-etching techniques.

In addition to the above-described structural design, the channels and the recesses of the micromechanically produced microdosing device according to the present invention can also be structured in Pyrex™ glass instead of being structure in silicon; also a combination of structuring in silicon and in Pyrex™ glass can be used for realizing the channels and recesses. The magnitude of the determinative parameters, flow resistance, fluidic inductance and capillary pressure, is determined by the length and the etched depth of the channels. The etched depths of the two channels and of the pressure chamber can be varied independently of one another by a multimask process.

As can be seen in FIG. 1, a membrane 16 having a central stiffened area is preferably used as a media displacer 10. The central stiffened area can then preferably be used as a surface for attaching the actuator 30. When a stiffened membrane is used as a media displacer 10, the dosing range can be adapted via the membrane width on the basis of a given displacement path of the actuator.

Making reference to FIG. 3, a dosing process according to a preferred embodiment of the present invention will be explained in detail in the following.

First of all, the arrangement, i.e. the fluid lines 20 and 22 and the pressure chamber 24 are filled for the first time either independently by capillary forces or by means of external support by applying pressure to the media reservoir, pumping in the medium or sucking in the liquid, e.g. by producing a vacuum at the outlet opening. At the location of outlet opening, or nozzle, a discharge of the medium is prevented by the surface tension, whereas a return flow of the medium in the direction of the dosing chamber is prevented by capillary forces, i.e. the meniscus of the liquid will automatically adjust itself to the position of the nozzle. After the first filling, which must, for example, only be carried out in the case of a first dosing process after a prolonged non-operative phase of the dosing device according to the present invention, the steps described hereinbelow will be carried out.

Figure 3:
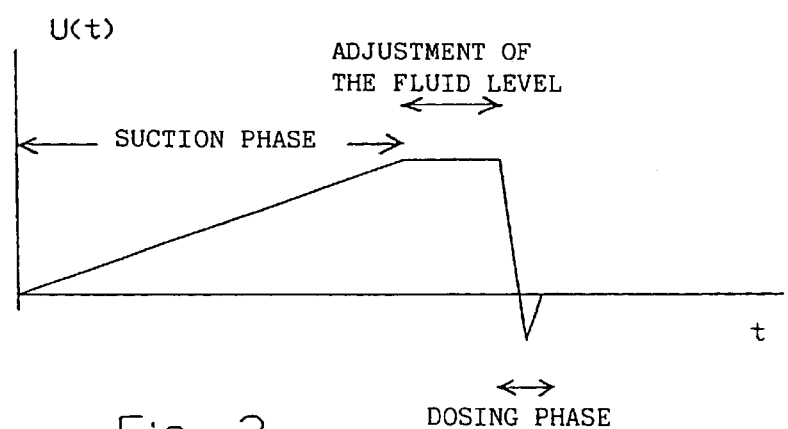
FIG. 3 shows a diagram showing a control signal for controlling the actuating device according to a preferred embodiment of the present invention.

During an interval referred to as suction phase in FIG. 3, a control signal, U(t), with low edge steepness is first applied to the actuating device. This has the effect that the membrane moves slowly from its starting position whereby liquid to be dosed is sucked from both channels, i.e. nozzle side and reservoir side, into the dosing chamber. The low edge steepness of the control signal has the effect that little acceleration is imparted to the liquid to be dosed. Depending on the flow resistance and the capillary pressure of the individual channels, the membrane sucks different isubvolumes out of the two channels. The inertia of the liquid can be neglected due to the slow process. In this process it should, however, be taken care that the nozzle channel is not emptied completely, since air would then penetrate into the dosing chamber. This can be guaranteed by adapting the control of the actuator, i.e. the edge steepness of the control signal, to the relation between the flow resistances of the fluid line connected to the medium reservoir and of the fluid line connected to the nozzle. This slow-motion process of the membrane from the starting position is finished when the integrated volume sensor of the control means indicates that the desired volume position has been reached.

Subsequently, a phase which is referred to as "adjustment of the fluid level" takes place in the case of the embodiment shown in FIG. 3. This adjustment of the fluid meniscus to the nozzle end takes place automatically due to capillary forces and surface tensions when the displacer has reached the desired volume position. The duration of this process is determined by the flow resistance of the channels and perhaps by that of the dosing chamber—the flow resistance of the dosing chamber being, however, negligible in most cases in comparison with the flow resistance of the channels—the physical properties of the medium, i.e. the viscosity, and the hydrostatic pressure in the reservoir. This adjustment phase of the fluid level is optional, since it can be dispensed with, provided that the suction phase takes place in a sufficiently slow manner, the fluid meniscus being then always at the location of the nozzle.

In a third phase, which is referred to as "dosing phase" in FIG. 3, the displacer is returned very rapidly to its starting position by a suitable control of the actuating device with the aid of the control means. This is realized by a control signal which has a large edge steepness and which imparts a high acceleration to the liquid. This has the effect that liquid is ejected through the nozzle as a free jet. Under these circumstances, the movement of the liquid in the reservoir channel and in the nozzle channel is determined almost exclusively by the relation between the liquid inertias in the respective fluid lines, whereas the relation between the flow resistances is negligible. If the inertia of the liquid in the fluid line between the dosing chamber and the nozzle is small in comparison with the inertia of the liquid in the fluid line between the dosing chamber and the reservoir, the flow of liquid back into the reservoir is negligible. If the inertia of the liquid in the reservoir channel is, however, not negligible, the return flow resulting therefrom can be determined by a calibration and compensated for during a subsequent dosing process. This is possible in view of the fact that the inductance L, i.e. the inertia, of a fluid line depends only on the geometry data thereof, L=length of the line/cross-section of the line, but not on the physical properties of the liquid contained in the fluid line.

The ratio of the accelerated amounts of liquid in the direction of the nozzle and in the direction of the reservoir when the displacer changes rapidly, i.e. when flow resistances are neglected, is given by:

$$\frac{d\Phi_d}{d\Phi_r} = \frac{\frac{d\Phi_d}{dt}}{\frac{d\Phi_r}{dt}} = \frac{\frac{\Delta p_d}{\rho L_d}}{\frac{\Delta p_r}{\rho L_r}} = \frac{\Delta p_d L_r}{\Delta p_r L_d} \approx \frac{L_r}{L_d} \quad \text{(eq. 1)}$$

wherein $\Phi_d$ and $L_d$ stand for the volume flow and the inductance in the direction of the nozzle and $\Phi_r$ and $L_r$ stand for the volume flow and the inductance in the direction of the reservoir.

Normally the ambient pressure and the pressure in the reservoir, which can amount to some mbar, are both negligible in comparison with the pressures which are applied to the dosing chamber when the displacer changes rapidly and which can amount to several bar. Hence, the pressure differences $\Delta p_d$ and $\Delta p_r$ are almost identical, and, consequently, a fixed relation exists between the liquid flow amounts in the direction of the nozzle and in the return direction. This relation is independent of the viscosity and the density $\varrho$ of the liquid contained. Hence, the volume lost due to the return flow through the reservoir channel in the first phase of the dosing process, i.e. the slow movement of the displacer for increasing the pressure chamber volume, can simply be taken into account.

A possible overtravel of the displacer beyond the position of rest can be prevented e.g. by detecting with the aid of the control means the detected time-dependent signal of the volume sensor while the jet of liquid is being ejected and by analyzing this signal. This permits a controlling influence on the current dosing process, complicated electronics being, however, necessary for this purpose. Alternatively, the signal detected by the volume sensor can also be analyzed after the ejection process and it can be used for optimizing the control parameters of the actuating device during subsequent dosing cycles.

It follows that the control means of the microdosing device according to the present invention controls the actuating device on the basis of the signals received from the volume sensor, i.e. the sensor for detecting the position of the membrane, during a current cylce or on the basis of the sensor signals detected during at least one preceding cycle.

Figure 4:
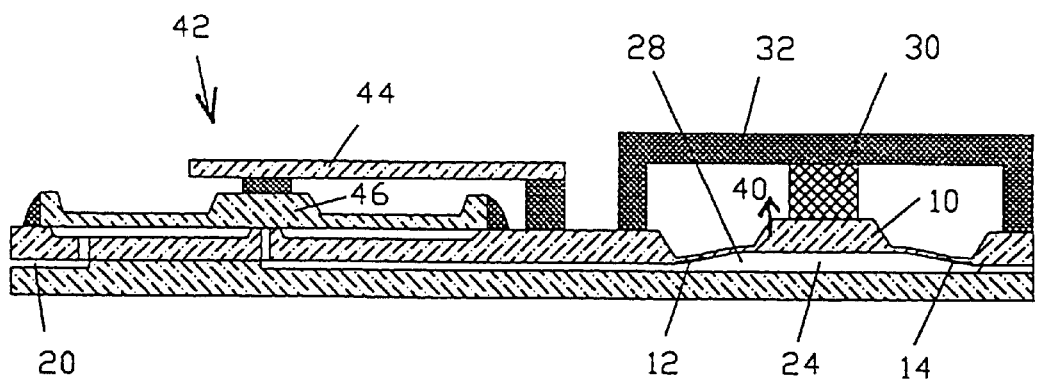
FIG. 4 shows a further embodiment of components of a microdosing device according to the present invention having a valve arranged in the reservoir channel.

FIG. 4 shows an alternative embodiment of a microdosing device according to the present invention in which a valve is arranged in the channel between the pressure chamber and the media reservoir. Elements corresponding to those in FIG. 1 are designated by identical reference numerals in FIG. 4. The arrow 40 in FIG. 4 indicates the movement of the media displacer 10 from the position of rest shown. As can be seen in FIG. 4, a valve, which is generally designated by reference numeral 42, is arranged so as to permit the fluid line 20 to be closed, the fluid line 20 being in fluid communication with the media reservoir (not shown). The valve 42 shown in FIG. 4 is a valve which is operable by means of an piezoelectric drive 44 and which is frequently used in the field of technology; in the case of this valve, the fluid line 20 can be closed by a membrane 46 which is adapted to be moved by means of the drive 44.

Alternatively to the embodiment shown in FIG. 4, any suitable active or passive valve can be used for preventing a return flow through the reservoir channel 20 while the jet of liquid is being ejected through the nozzle. Such a valve is not necessary when, as in the case of ink-jet printheads, the volume of the liquid flowing back in the direction of the reservoir can be neglected due to the higher inertia of the liquid. Furthermore, such a valve can be dispensed with when a fixed relation exists between the quantity of the liquid volume and the volume to be dosed and when this quantity can therefore be corrected via the volume displacement of the displacer, see above.

The movement of the displacer during ejection of the liquid can be carried out directly to the position of rest. Alternatively, the movement of the displacer during ejection of the liquid can be finished with a small countermovement, this being again shown in FIG. 3, cf. the end of the dosing phase. Due to this countermovement, a counteracceleration occurs which can support the interruption of the jet of liquid.

Figure 5A:
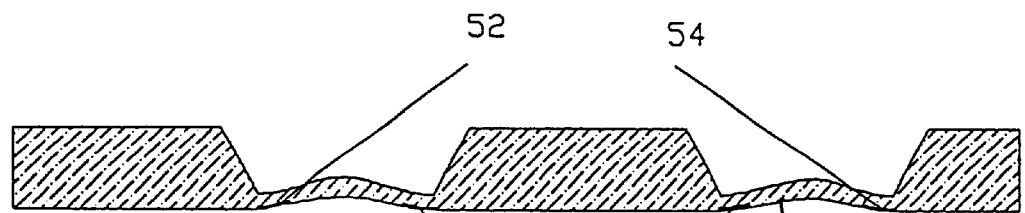
FIGS. 5A and 5B show schematic cross-sectional representations of a displacer for additional pressure detection.
Figure 5B:
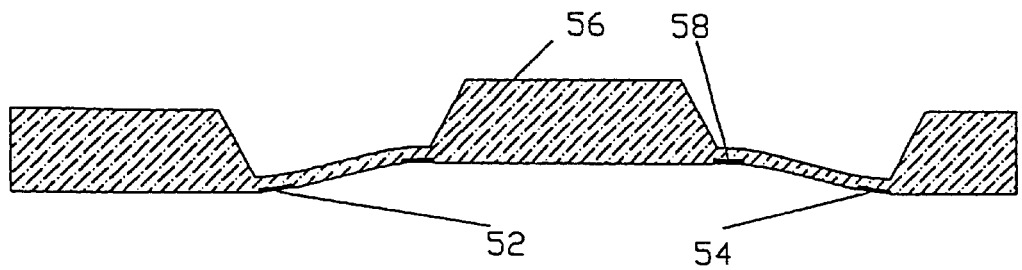

Making reference to FIG. 5A and 5B, an alternative embodiment of a media displacer will be described in detail in the following. The volume displacement of the media displacer and the pressure in the dosing chamber are two independent physical parameters. It follows that, by positioning and interconnecting a plurality of different resistors in the membrane suspension of the displacer in a suitable manner, either the volume position of the displacer can be measured independently of the pressure or the pressure in the dosing chamber can be measured independently of the volume. Such an arrangement of piezoresistive resistors is shown in FIG. 5A and 5B. Four piezoresistive resistors 52, 54, 56 and 58 are implemented in the suspension 50 of the membrane. FIG. 5A shows the mechanical deformation of the membrane in the case of an overpressure in the dosing chamber, the displacer volume being negligible. FIG. 5B shows the mechanical deformation of the membrane in the case of a displacement at vanishing pressure, e.g. at the end of the above-described phase "adjustment of the fluid level".

Although the signals of the respective outer resistors are almost identical, the two cases differ with regard to the signals of the mechanical stresses close to the central stiffened area of the membrane. In the case shown in FIG. 5A, tensile stresses act on each of the four piezoresistive resistors. In the case shown in FIG. 5B, tensile stresses act on the piezoresistive resistors 52 and 54, whereas compressive stresses act on the piezoresistive resistors 56 and 58. Tensile stresses are produced by the pressure in the dosing chamber, whereas pure volume deformations produce compressive stresses. When the piezoresistive effect is used, this will find expression in different signs when there is a change of resistance. On the basis of a suitable positioning and evaluation of the resistors, the two physical quantities, i.e. pressure and volume, can therefore be determined independently of one another. Thus, the piezoresistive resistors 52, 54, 56 and 58 form means for detecting the pressure in said pressure chamber.

In the following, further alternative embodiments of the microdosing device according to the present invention will be explained. In the initial state of the dosing cycle, the displacer can be pretensioned and held by the actuator at this position, e.g. forced into the dosing chamber. The displacer can in this case be moved in the direction of a further pretension by an additional displacement of the actuator. When the actuator displacement decreases, the displacer will move in the direction opposite to the direction of pretension due to its restoring force alone. Making use of this variant, no fixed connection between the actuator and the displacer is required. A possible adhesive connection between the actuator and the displacer can be dispensed with and the assembly work required is essentially reduced. With regard to the volume sensor integrated in the displacer, it will only be necessary to correct the volume offset caused by the pretension.

Figure 6A:
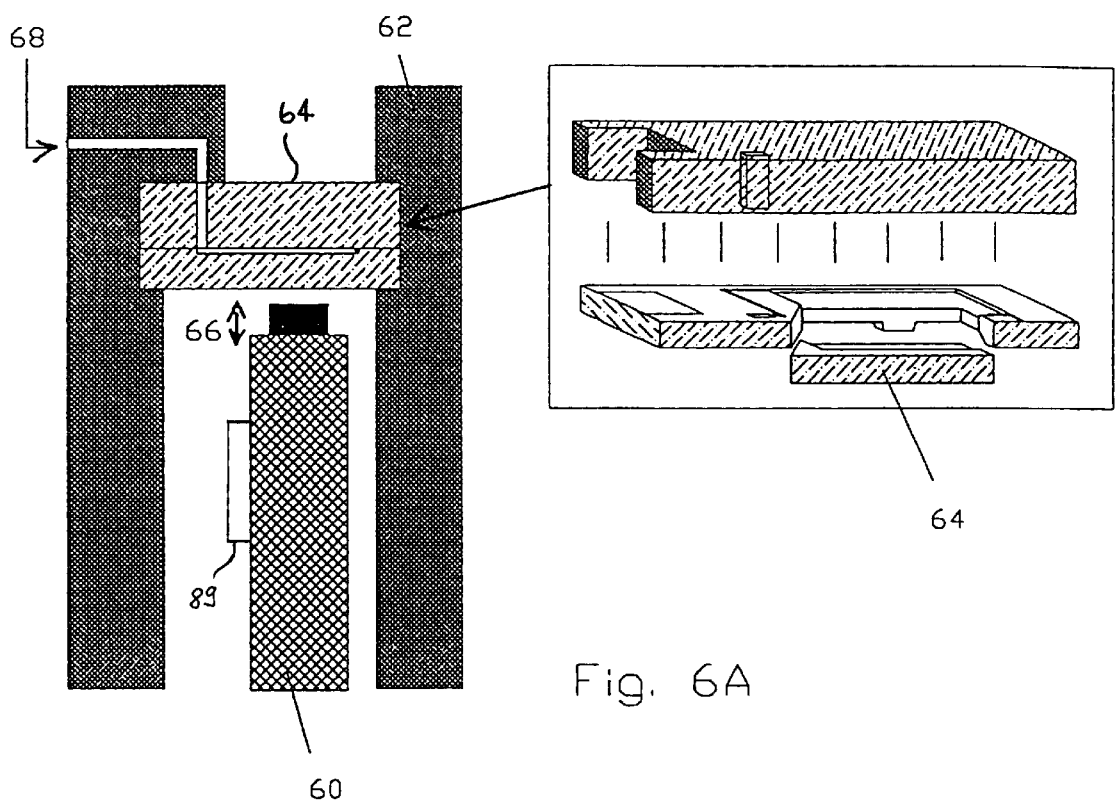
FIGS. 6A and 6B show schematic representations of embodiments for realizing the microdosing device according to the present invention.
Figure 6B:
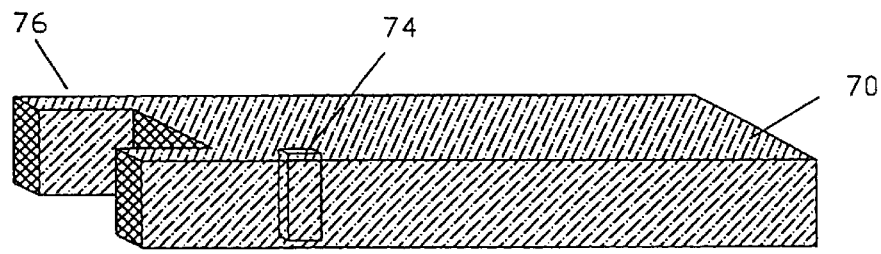
Figure 6B:
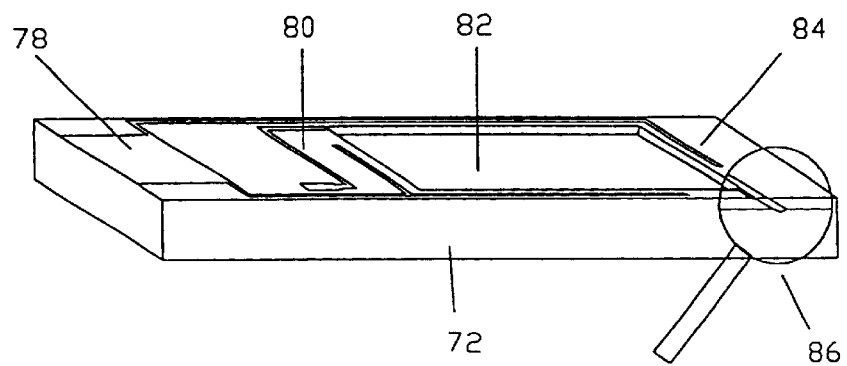

The above-described alternative of using the actuator and the displacer without any fixed connection permits a modular structural design of the dosing element. Such a structural design is shown in FIGS. 6A and 6B for the purpose of illustration. The electronics and the drive, e.g., a piezostract actuator 60, and are fixedly installed in a housing 62, whereas a chip 64 comprising the media displacer and the sensors is replaceable. The arrow 66 in FIG. 6A indicates the direction of movement of the piezo-stack actuator. Furthermore, a fluid line 68, which extends through the housing, is shown in FIG. 6A. The part of FIG. 6A on the right-hand side shows an enlargement of the micromechanically produced components of the microdosing device, the Pyrex™ plate and the silicon chip being shown separately.

An enlargement of this micromechanically produced components of the microdoing device is shown, in drawn-apart form, in FIG. 6B. These components are defined by a Pyrex™ plate 70 which is connected to a silicon chip 72 e.g. by means of anodic bonding. A fluid line 74, which is in fluid communication with a media reservoir (not shown), extends through the Pyrex™ glass plate 70. The Pyrex™ glass plate 70 additionally includes a recess 76 so as to permit electric contacting of terminal areas 78 and the silicon chip. The reservoir channel is shown with 80, whereas the dosing chamber is shown with 82. The silicon chip 72 has additionally provided thereon conductor paths 84 leading to the volume sensors. By means of a further enlargement 86, the outlet end or the nozzle of the microdosing device is schematically shown in FIG. 6B.

In the modular configuration described, it will be advantageous when no adhesive connection between the actuator and the displacer is necessary, but only a mechanical contact for producing a pretension, as has been described hereinbefore. Via the signal of the integrated volume sensors, it is also possible to adjust the pretension in a reproducable manner and with high accuracy.

In the case of all the embodiments described, non-linearities and e.g. hysteresis effects, which occur when the displacer is being driven, can be compensated for by the integrated volume sensor. Furthermore, it will be advantageous to coat the nozzle with a hydrophobic material, since this will increase the surface tension whereby a flow of liquid out of the nozzle in the inoperative state will be suppressed still further. In this respect, it will be particularly advantageous to provide a coating of hydrophobic material outside of the nozzle in the neighbourhood along the circumference of the nozzle.

Alternatively to the described volume sensors in the media displacer, the volume sensor can also be integrated in the actuating device for the displacer. The volume sensor can, for example, be realized as a strain gauge on the piezostack actuator, the strain gauge detecting the displacement of the piezo-stack actuator. A strain gauge 89 is schematically shown in FIG. 6A.

As has already been mentioned, the microdosing device according to the present invention can also be used as a pipetting device. For this purpose, the microdosing device is preferably provided with a means for producing a partial vacuum in the media reservoir so as to permit a liquid to be sucked into the dosing chamber and/or the media reservoir through the outlet opening by immersing the outlet opening, i.e. the nozzle, into a liquid to be pipetted. The liquid to be pipetted can, however, also be sucked into the dosing chamber by a suitable movement of the actuator and, consequently, of the displacer, the provision of the media reservoir and of the fluid line between the media reservoir and the dosing chamber being then not necessary. With regard to the other features and the implementation thereof, the pipetting device corresponds to the microdosing device according to the present invention, the control means controlling the actuating device, i.e. the actuator, on the basis of the signals from the sensor for detecting the position of the displacer during the current pipetting cycle or on the basis of the sensor signals during at least one preceding cycle so as to cause a defined fluid volume to be sucked in and/or discharged from the outlet opening.

The outlet opening of the devices according to the present invention can, alternatively, be implemented as a nozzle array consisting of e.g. 10 nozzles. An array of jets of liquid can be produced in this way, each individual jet containing only one tenth of the whole dosing volume. The functionality of so-called multi-channel pipettes is obtained in this way, these multi-channel pipettes being used for dosing into so-called microtitration plates. Furthermore, in comparison with the use of a large nozzle, the use of a plurality of small nozzles results in a larger capillary force acting on the discharge side, whereby a return flow will be reduced in cases in which a signal of low edge steepness is used as a control signal.

In addition to the described planar arrangement of nozzle and chip, the nozzle can also be arranged vertically relative to the chip in alternative embodiments of the present invention, the fluid being then discharged from the nozzle at right angles to the chip. A vertical arrangement is adavantageous insofar as the dosing device, i.e. the actuator, the chip and the nozzle, can have an axial structural design; this corresponds to the habit of the users of e.g. conventional pipettes.

In the following, a simplified description of the dynamics of the dosing process will be given. In so doing, a flow resistance is defined as R and a fluidic inductance as L. The pressure drop across a flow channel is composed of a pressure drop $\Delta p_{laminar}$, which serves to overcome the flow resistance, and a pressure drop $\Delta p_{inert}$, which accelerates the fluid in the channel. Hence, the following holds true for the pressure difference $\Delta p_{line}$ over the whole fluid line:

$$\Delta P_{line} = \Delta p_{laminar} + \Delta p_{inert}$$
$$\Delta P_{inert} = \varrho L \, (d\Phi/dt) \text{ with } L = l/A$$
$$\Delta P_{laminar} = \varrho R \Phi \qquad \text{(eq. 2)}$$

The flow resistance R and the fluidic inductance L are calculated e.g. for a round hose having the radius r as follows:

$$L = \frac{l}{r^2 \pi}; \quad R = \frac{8\eta l}{\rho \pi r^4} \qquad \text{(eq. 3)}$$

Figure 7:
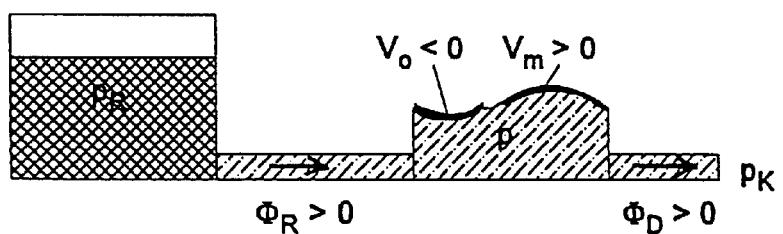
FIG. 7 shows a scheme in which essential parameters of the method according to the present invention are shown.

FIG. 7 shows a scheme for describing the dynamics of a microdosing device according to the present invention. $p_R$ stands for the pressure in the media reservoir, $p_K$ stands for the capillary pressure and p for the pressure in the pressure chamber. $V_m$ corresponds to the volume displaced by the membrane, whereas $V_0$ corresponds to the change of the chamber volume caused by strain on the housing and other perturbing influences. $\Phi_r$ is the volume flow in the reservoir channel and $\Phi_D$ is the flow in the nozzle channel. In the equations following hereinbelow, U corresponds to the control voltage at the actuator.

The following holds true for the fluid line between the dosing chamber and the reservoir:

$$p_R - p = \rho R_R \Phi_R + \rho L_R \frac{d\Phi_R}{dt} \qquad \text{(eq. 4)}$$

The following holds true for the fluid line between the dosing chamber and the nozzle:

$$p + p_k - p_{atmosphere} = \rho R_D \Phi_D + \rho L_D \frac{d\Phi_D}{dt} \qquad \text{(eq. 5)}$$

The following holds true for the dosing chamber:

$$\frac{dV}{dt} = \Phi_R - \Phi_D$$

-continued $$\frac{d}{dt}(V_m + V_o) = \frac{\partial V_m}{\partial p}\bigg|_U \frac{dp}{dt} + \frac{\partial V_m}{\partial U}\bigg|_p \frac{dU}{dt} + \frac{\partial V_o}{\partial p}\frac{dp}{dt}$$

$$= \Phi_R - \Phi_D$$

and, consequently, $$\frac{dp}{dt} = \frac{\Phi_R - \Phi_D - \frac{\partial V_m}{\partial U}\bigg|_p \frac{dU}{dt}}{\frac{\partial V_m}{\partial p}\bigg|_U + \frac{\partial V_o}{\partial p}} \quad \text{(eq. 6)}$$

Summarizing it can be stated that the dynamics of the dosing element is approximately described by three differential equations for the three independent variables $\Phi_r$, $\Phi_D$ and p as follows:

$$\frac{dp}{dt} = \frac{\Phi_R - \Phi_D - \frac{\partial V_m}{\partial U}\bigg|_p \frac{dU}{dt}}{\frac{\partial V_m}{\partial p}\bigg|_U + \frac{\partial V_o}{\partial p}} \quad \text{(eq. 7)}$$

$$\frac{d\Phi_R}{dt} = \frac{p_R - p - \rho R_R \Phi_R}{\rho L_R}$$

$$\frac{d\Phi_D}{dt} = \frac{p + p_K - \rho R_D \Phi_D}{\rho L_D}$$

The following predetermined design parameters are known: $R_R$, $R_D$, $L_R$, $L_D$. Operating parameters are the voltage U(t) and the media reservoir pressure $p_R$. The quantity to be measured is the pressure $p_K$ and the quantities to be measured or to be calculated are $dV_m/d_p$, $dV_0/d_p$, and $dV_m/dU$.

The differential equation system is to be solved for a predetermined U(t) for the following boundary conditions:

p(t=0)=0;
$\Phi_R$(t=0)=0; and
$\Phi_D$(t=0)=0.

A microdosing device array can be composed of a plurality of microdosing devices according to the present invention, which are arranged in an arraylike configuration. The microdosing devices can, for example, be arranged in parallel juxtaposed relationship with one another. It is then possible to arrange e.g. four nozzles within an area of less than one square millimetre and to address these nozzles individually. Each microdosing device discharges separately from the other ones a medium in the form of a free jet so that different media can be discharged. On the basis of the arrangement of the plurality of microdosing devices, it is then possible that the separately discharged media mix in the air after having left the array of microdosing devices. It follows that the array of microdosing devices provides very versatile possibilities of dosing pure media as well as a mixture of media. When a mixture is being dosed, the individual media components can be dosed exactly by the individual microdosing devices.

Figure 8:
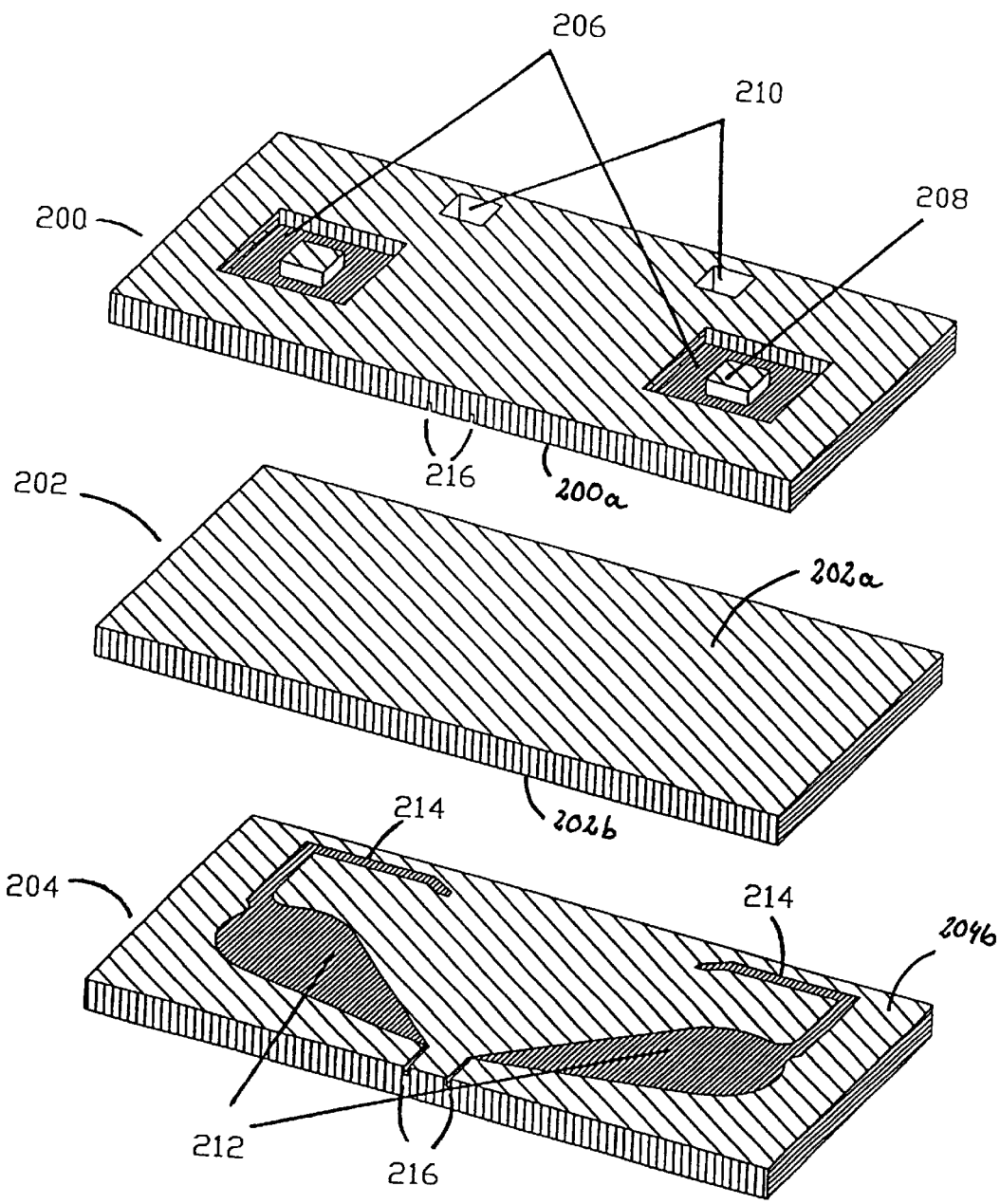
FIG. 8 shows a drawn-apart schematic representation of an embodiment of an array of microdosing devices composed of a plurality of microdosing devices according to the present invention.
Figure 9:
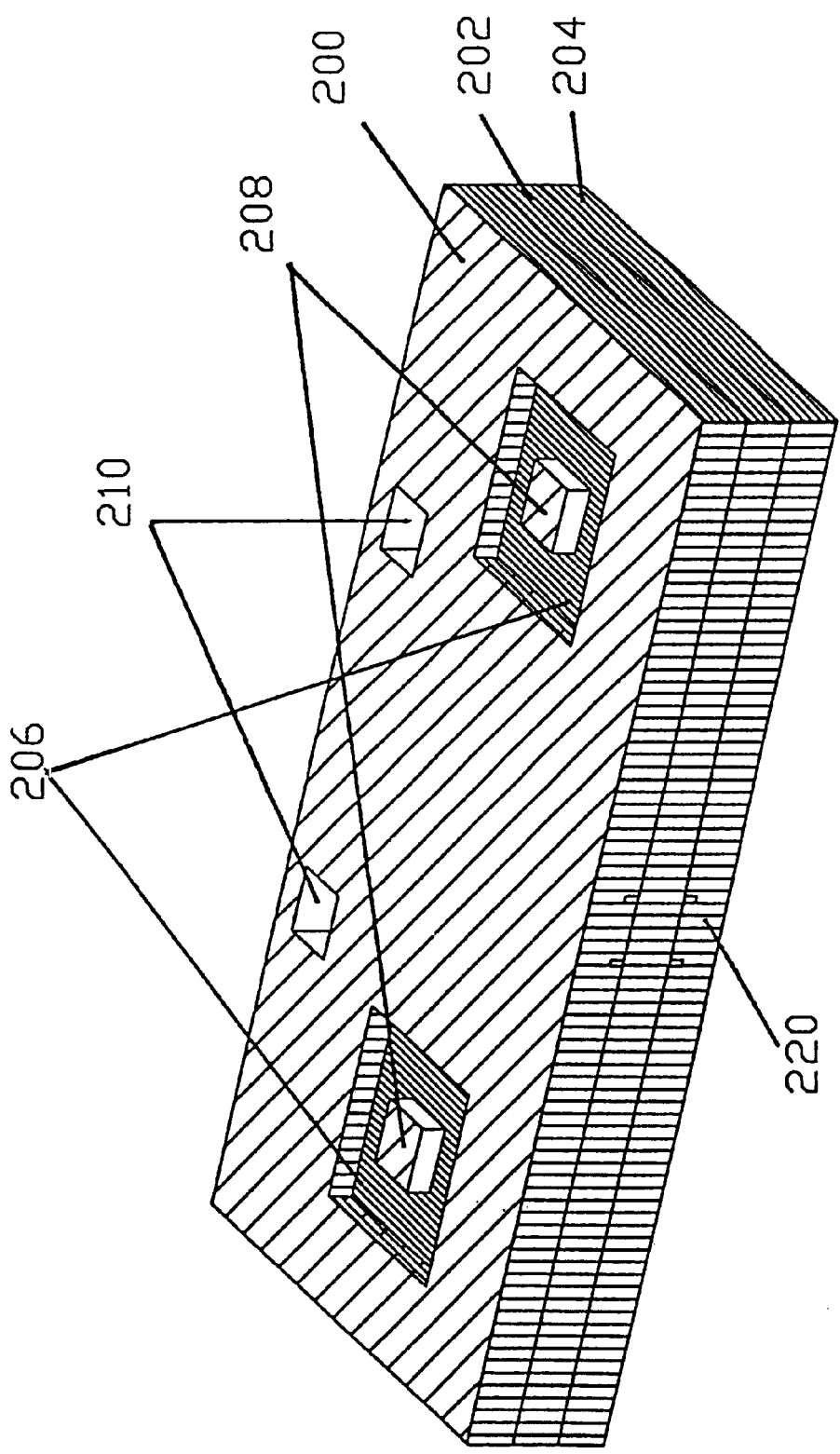
FIG. 9 shows a schematic representation of the array of microdosing devices, which is shown in FIG. 8, in the assembled state.

An embodiment of a microdosing device according to the present invention is shown in FIG. 8 and 9.

As can be seen in FIG. 8, an array of microdosing devices according to the present invention can be formed of a structure comprising a first silicon layer 200, a Pyrex™ glass plate 202 and a second silicon layer 204. In the embodiment shown, the structures for two microdosing devices are formed in the first silicon layer 200. For this purpose, two displacer membranes 206, which are each provided with a stiffened area 208, are formed in the silicon layer 200. The displacer membranes 206 are adapted to be actuated via the stiffened areas 208. Furthermore, fluid channels 210, which connect the pressure chamber to a media reservoir (not shown), are arranged in the first silicon layer.

The structural design of the second silicon layer 204 is substantially identical to that of the first silicon layer 200. In FIG. 8, the surface of the second silicon layer 204 which is opposed to the surface of the first layer 200 shown in this FIG. 8 can be seen. It follows that, with regard to the second silicon layer 204, the pressure chambers 212 formed in this silicon layer 204 and the fluid lines 214 connecting the pressure chambers 212 to a media reservoir can be seen. The fluid lines 214 of a respective silicon layer end in the fluid channels 210 of the respective layer. FIG. 8 also shows fluid lines which connect the pressure chambers to the respective outlet opening 216.

The Pyrex™ glass plate 202 is arranged between the two silicon layers 200 and 204 in such a way that the respective main surfaces (202*a*, 202*b*) thereof are connected to the main surfaces 200*a* and 204*b* of the first and of the second silicon layer in which the pressure chambers 212 are formed. The respective pressure chambers and fluid lines are therefore defined by the structures in the silicon layers and the surfaces of the Pyrex™ glass plate.

The thus formed structure, which is shown in FIG. 9, is provided with an array of nozzles 220 defined by the four outlet openings 216 in the first and in the second silicon wafer. Each nozzle of the 2×2 array 220 has associated therewith a displacer membrane 206 with an associated actuating device (not shown in FIG. 8 and 9) so that the nozzles can be addressed individually.

It is apparent that, making use of the above-described structural design, microdosing device arrays comprising an almost arbitrary number of microdosing devices can be constructed. In addition, it is apparent that the fluid channels of the respective pressure chambers can be connected either to the same or to different media reservoirs. Furthermore, an array of pipetting devices can be constructed in a corresponding manner making use of a plurality of pipetting devices according to the present invention.

What is claimed is:

1. A microdosing device comprising:
   a pressure chamber which is at least partly delimited by a displacer;
   an actuating device for actuating the displacer, the volume of the pressure chamber being adapted to be changed by actuating the displacer,
   a media reservoir which is in fluid communication with the pressure chamber via a first fluid line;
   an outlet opening which is in fluid communication with the pressure chamber via a second fluid line;
   a means for detecting the position of the displacer; and
   a control means which is connected to the actuating device and to the means for detecting the position of the displacer and which controls the actuating device on the basis of the detected position of the displacer or on the basis of displacer positions detected during at least one preceding dosing cycle so as to cause the discharge of a defined volume of fluid from the outlet opening,
   wherein the control means comprises means for controlling the actuating device with a signal of low edge steepness so as to cause the displacer to move from a first position to a predetermined second position, said second position of the displacer defining a larger volume of the pressure chamber than said first position; and that the control means comprises means for controlling the actuating device with a signal of high edge steepness so as to cause the displacer to move from the second position to the first position for discharging in this way a defined volume of fluid from the outlet opening.

2. A microdosing device according to claim 1, wherein an active or a passive valve is arranged in the fluid line between the media reservoir and the pressure chamber, said valve being used for preventing a return flow of fluid from the pressure chamber to the media reservoir.

3. A microdosing device according to claim 1, wherein the pressure chamber, the displacer and the means for detecting the position of the displacer are implemented as micromechanically produced structures.

4. A microdosing device according to claim 3, wherein the displacer is realized as a stiffened membrane etched in a silicon wafer, and wherein the means for detecting the position of the displacer is realized by piezoresistive elements provided in or on the membrane.

5. A microdosing device according to claim 4, wherein at least parts of the first and second fluid lines, the outlet opening and the pressure chamber are defined by structures in the silicon wafer and/or a borosilicate glass plate connected to said silicon wafer.

6. A microdosing device according to claim 1, wherein the pressure chamber has additionally arranged therein means for detecting the pressure in said pressure chamber.

7. A microdosing device according to claim 3, wherein the actuating device is a piezo-stack actuator, said means for detecting the position of the displacer being realized by a strain gauge provided on the piezo-stack actuator.

8. A microdosing device according to claim 1, wherein the outer surround of the outlet opening is coated with a hydrophobic material.

9. A microdosing device according to claim 3, wherein the actuating device and the control means are fixedly installed in a housing, whereas the pressure chamber, the displacer and the means for detecting the position of the displacer are adapted to be replaceably installed in the housing.

10. A microdosing device according to claim 1, wherein the outlet opening is formed by an array comprising a plurality of openings.

11. A microdosing device array consisting of a plurality of microdosing devices arranged side by side and adapted to be addressed individually, said microdosing devices comprising:
   a pressure chamber which is at least partly delimited by a displacer;
   an actuating device for actuating the displacer, the volume of the pressure chamber being adapted to be changed by actuating the displacer,
   a media reservoir which is in fluid communication with the pressure chamber via a first fluid line;
   an outlet opening which is in fluid communication with the pressure chamber via a second fluid line;
   a means for detecting the position of the displacer; and
   a control means which is connected to the actuating device and to the means for detecting the position of the displacer and which controls the actuating device on the basis of the detected position of the displacer or on the basis of displacer positions detected during at least one preceding dosing cycle so as to cause the discharge of a defined volume of fluid from the outlet opening, wherein the control means comprises means for controlling the actuating device with a signal of low edge steepness so as to cause the displacer to move from a first position to a predetermined second position, said second position of the displacer defining a larger volume of the pressure chamber than said first position; and
   that the control means comprises means for controlling the actuating device with a signal of high edge steepness so as to cause the displacer to move from the second position to the first position for discharging in this way a defined volume of fluid from the outlet opening.

12. A microdosing device array according to claim 11, wherein the pressure chambers, the displacers and the fluid lines of a first number of microdosing devices are formed by a first silicon layer having a main surface thereof connected to a first main surface of a glass plate, whereas the pressure chambers the displacers and the fluid lines of a second number of microdosing devices are formed by a second silicon layer having a main surface thereof connected to the second main surface of the glass plate.

13. A pipetting device comprising:
   a pressure chamber which is at least partly delimited by a displacer;
   an actuating device for actuating the displacer, the volume of the pressure chamber being adapted to be changed by actuating the displacer,
   an outlet opening which is in fluid communication with the pressure chamber via a fluid line;
   a means for detecting the position of the displacer; and
   a control means which is connected to the actuating device and to the means for detecting the position of the displacer and which controls the actuating device on the basis of the detected position of the displacer or on the basis of displacer positions detected during at least one preceding pipetting cycle so as to cause a defined volume of fluid to be sucked in through and/or discharged from the outlet opening, wherein
      the control means comprises means for controlling the actuating device with a signal of low edge steepness so as to cause the displacer to move from a first position to a predetermined second position, said second position of the displacer defining a larger volume of the pressure chamber than said first position, and
      the control means comprises means for controlling the actuating device with a signal of high edge steepness so as to cause the displacer to move from the second position to the first position for discharging in this way a defined volume of fluid from the outlet opening.

14. A pipetting device according to claim 13, comprising in addition a media reservoir which is in fluid communication with the pressure chamber via a further fluid line.

15. A pipetting device array consisting of a plurality of pipetting devices arranged side by side and adapted to be addressed individually, said pipetting devices comprising:
   a pressure chamber which is at least partly delimited by a displacer,
   an actuating device for actuating the displacer, the volume of the pressure chamber being adapted to be changed by actuating the displacer,
   an outlet opening which is in fluid communication with the pressure chamber via a fluid line;
   a means for detecting the position of the displacer; and
   a control means which is connected to the actuating device and to the means for detecting the position of the displacer and which controls the actuating device on the basis of the detected position of the displacer or on the basis of displacer positions detected during at least one preceding pipetting cycle so as to cause a defined volume of fluid to be sucked in through and/or discharged from the outlet opening, wherein the control means comprises means for controlling the actuating device with a signal of low edge steepness so as to cause the displacer to move from a first position to a predetermined second position, said second position of the displacer defining a larger volume of the pressure chamber than said first position, and the control means comprises means for controlling the actuating device with a signal of high edge steepness so as to cause the displacer to move from the second position to the first position for discharging in this way a defined volume of fluid from the outlet opening.

16. A method of operating the microdosing device according to claim 1, comprising a) controlling the actuating device with a signal of low edge steepness so as to cause the displacer to move from a first position to a predetermined second position, said second position of the displacer defining a larger volume of the pressure chamber than said first position;

b) controlling the actuating device with a signal of high edge steepness so as to cause the displacer to move from the second position to the first position for discharging in this way a defined volume of fluid from the outlet opening.

17. A method according to claim 16, wherein, prior to step a), a step is carried out in which the fluid lines and the pressure chamber are filled with a fluid from the media reservoir.

18. A method according to claim 16, wherein, after step a), the control signal for the actuating device is held on a level for a predetermined period of time, said signal level causing the displacer to remain at the second position.

19. A method according to claim 16, wherein, in step b), the actuating device is controlled in such a way that the displacer, when moving to the first position, is initially moved beyond said first position by means of said actuating device before it finally reaches said first position.

20. A method according to claim 16, wherein, during control of the actuating device in step a), a return flow through the first fluid line during step b) is compensated for with the aid of the control means so that a defined volume of fluid will be discharged in step b).

21. A method according to claim 16, wherein the displacer, when at its first position, occupies a pretensioned position in such a way that, due to the control of the actuating device in step a), the displacer will be moved to the second position by a restoring force.

* * * * *